(12) United States Patent
Goodson, IV et al.

(10) Patent No.: US 8,518,011 B2
(45) Date of Patent: Aug. 27, 2013

(54) SHEATH FOR USE IN PERIPHERAL INTERVENTIONS

(75) Inventors: Harry B. Goodson, IV, Fremont, CA (US); Craig A. Ball, San Carlos, CA (US); Jeffrey M. Elkins, Woodside, CA (US)

(73) Assignee: AngioDynamics, Inc., Latham, NY (US)

( * ) Notice: Subject to any disclaimer, the term of this patent is extended or adjusted under 35 U.S.C. 154(b) by 437 days.

(21) Appl. No.: 12/549,486

(22) Filed: Aug. 28, 2009

(65) Prior Publication Data

US 2009/0318857 A1 Dec. 24, 2009

Related U.S. Application Data

(62) Division of application No. 11/073,421, filed on Mar. 4, 2005, now abandoned.

(60) Provisional application No. 60/550,632, filed on Mar. 4, 2004, provisional application No. 60/550,774, filed on Mar. 5, 2004.

(51) Int. Cl.
*A61M 31/00* (2006.01)

(52) U.S. Cl.
USPC .......................................... 604/508

(58) Field of Classification Search
USPC .................. 604/27, 28, 93.01, 171, 173, 264, 604/284, 506–510, 523, 532, 544
See application file for complete search history.

(56) References Cited

U.S. PATENT DOCUMENTS

| | | | |
|---|---|---|---|
| 1,696,018 A | 12/1928 | Schellberg | |
| 2,499,045 A | 2/1950 | Walker et al. | |
| 3,144,868 A | 8/1964 | Jascalevich | |
| 3,455,298 A | 7/1969 | Anstadt | |
| 3,516,408 A | 6/1970 | Montanti | |
| 3,667,069 A | 6/1972 | Blackshear et al. | |
| 3,730,186 A | 5/1973 | Edmunds, Jr. et al. | |

(Continued)

FOREIGN PATENT DOCUMENTS

| | | |
|---|---|---|
| DE | 43 24 637 | 3/1995 |
| EP | 0 654 283 A1 | 5/1995 |

(Continued)

OTHER PUBLICATIONS

"FDA Form 510(K) on related correspondence for Advanced Equipment Development, Inc.".

(Continued)

*Primary Examiner* — Kami A Bosworth
(74) *Attorney, Agent, or Firm* — Peter J. Flora

(57) ABSTRACT

A dual lumen introducer sheath provides access to at least one renal artery and at least one peripheral blood vessel of a patient. The introducer sheath includes a proximal hub comprising first and second ports, a first lumen, and a second lumen. The first lumen extends from the first port to a first distal aperture and has sufficient length such that when the first port is positioned outside the patient the first distal aperture is positionable in the abdominal aorta at or near origins of the patient's renal arteries. The second lumen extends from the second port to a second distal aperture, has a shorter length than the length of the first lumen, and is configured to allow passage of a catheter device through the second lumen and into or through an iliac artery contralateral to an insertion point of the introducer sheath into the patient.

7 Claims, 5 Drawing Sheets

(56) References Cited

U.S. PATENT DOCUMENTS

| | | |
|---|---|---|
| 3,791,374 A | 2/1974 | Guarino |
| 3,841,331 A | 10/1974 | Wilder et al. |
| 3,995,623 A | 12/1976 | Blake et al. |
| 4,248,224 A | 2/1981 | Jones |
| 4,309,994 A | 1/1982 | Grunwald |
| 4,345,602 A | 8/1982 | Yoshimura et al. |
| 4,407,271 A | 10/1983 | Schiff |
| 4,423,725 A | 1/1984 | Baran et al. |
| 4,459,977 A | 7/1984 | Pizon et al. |
| 4,490,374 A | 12/1984 | Bandurco et al. |
| 4,493,697 A | 1/1985 | Krause et al. |
| 4,536,893 A | 8/1985 | Parravicini |
| 4,546,759 A | 10/1985 | Solar |
| 4,554,284 A | 11/1985 | Stringer et al. |
| 4,636,195 A | 1/1987 | Wolinsky |
| 4,685,446 A | 8/1987 | Choy |
| 4,705,502 A | 11/1987 | Patel |
| 4,705,507 A | 11/1987 | Boyles |
| 4,712,551 A | 12/1987 | Rayhanabad |
| 4,714,460 A | 12/1987 | Calderon |
| 4,723,939 A | 2/1988 | Anaise |
| 4,753,221 A | 6/1988 | Kensey et al. |
| 4,781,716 A | 11/1988 | Richelsoph |
| 4,817,586 A | 4/1989 | Wampler |
| 4,834,707 A | 5/1989 | Evans |
| 4,840,172 A | 6/1989 | Augustine et al. |
| 4,846,831 A | 7/1989 | Skillin |
| 4,861,330 A | 8/1989 | Voss |
| 4,863,461 A | 9/1989 | Jarvik |
| 4,888,011 A | 12/1989 | Kung et al. |
| 4,902,272 A | 2/1990 | Milder et al. |
| 4,902,291 A | 2/1990 | Kolff |
| 4,906,229 A | 3/1990 | Wampler |
| 4,909,252 A | 3/1990 | Goldberger |
| 4,911,163 A | 3/1990 | Fina |
| 4,919,647 A | 4/1990 | Nash |
| 4,925,377 A | 5/1990 | Inacio et al. |
| 4,925,443 A | 5/1990 | Heilman et al. |
| 4,927,407 A | 5/1990 | Dorman |
| 4,927,412 A | 5/1990 | Menasche |
| 4,938,766 A | 7/1990 | Jarvik |
| 4,950,226 A | 8/1990 | Barron |
| 4,957,477 A | 9/1990 | Lundback |
| 4,964,864 A | 10/1990 | Summers et al. |
| 4,976,691 A | 12/1990 | Sahota |
| 4,976,692 A | 12/1990 | Atad |
| 4,990,139 A | 2/1991 | Jang |
| 4,995,864 A | 2/1991 | Bartholomew et al. |
| 5,002,531 A | 3/1991 | Bonzel |
| 5,002,532 A | 3/1991 | Gaiser et al. |
| 5,044,369 A | 9/1991 | Sahota |
| 5,053,023 A | 10/1991 | Martin |
| 5,059,178 A | 10/1991 | Ya |
| 5,067,960 A | 11/1991 | Grandjean |
| 5,069,662 A | 12/1991 | Bodden |
| 5,069,680 A | 12/1991 | Grandjean |
| 5,073,094 A | 12/1991 | Dorman et al. |
| 5,087,244 A | 2/1992 | Wolinsky |
| 5,089,019 A | 2/1992 | Grandjean |
| 5,098,370 A | 3/1992 | Rahat et al. |
| 5,098,442 A | 3/1992 | Grandjean |
| 5,112,301 A | 5/1992 | Fenton, Jr. et al. |
| 5,112,349 A | 5/1992 | Summers et al. |
| 5,119,804 A | 6/1992 | Anstadt |
| 5,129,883 A | 7/1992 | Black |
| 5,131,905 A | 7/1992 | Grooters |
| 5,135,474 A | 8/1992 | Swan et al. |
| 5,158,540 A | 10/1992 | Wijay et al. |
| 5,160,323 A | 11/1992 | Andrew |
| 5,163,910 A | 11/1992 | Schwartz et al. |
| 5,167,628 A | 12/1992 | Boyles |
| 5,180,364 A | 1/1993 | Ginsburg |
| 5,205,810 A | 4/1993 | Guiraudon et al. |
| 5,226,888 A | 7/1993 | Arney |
| 5,256,141 A | 10/1993 | Gencheff et al. |
| 5,257,974 A | 11/1993 | Cox |
| 5,282,784 A | 2/1994 | Willard |
| 5,290,227 A | 3/1994 | Pasque |
| 5,292,309 A | 3/1994 | Van Tassel et al. |
| 5,308,319 A | 5/1994 | Ide et al. |
| 5,308,320 A | 5/1994 | Safar et al. |
| 5,312,343 A | 5/1994 | Krog et al. |
| 5,320,604 A | 6/1994 | Walker et al. |
| 5,326,374 A | 7/1994 | Ilbawi et al. |
| 5,328,470 A | 7/1994 | Nabel et al. |
| 5,332,403 A | 7/1994 | Kolff |
| 5,345,927 A | 9/1994 | Bonutti |
| 5,358,519 A | 10/1994 | Grandjean |
| 5,364,337 A | 11/1994 | Guiraudon et al. |
| 5,370,617 A | 12/1994 | Sahota |
| 5,383,840 A | 1/1995 | Heilman et al. |
| 5,389,090 A | 2/1995 | Fischell et al. |
| 5,397,307 A | 3/1995 | Goodin |
| 5,405,341 A | 4/1995 | Martin |
| 5,411,479 A | 5/1995 | Bodden |
| 5,421,826 A | 6/1995 | Crocker et al. |
| 5,429,584 A | 7/1995 | Chiu |
| 5,453,084 A | 9/1995 | Moses |
| 5,464,449 A | 11/1995 | Ryan et al. |
| 5,476,453 A | 12/1995 | Mehta |
| 5,478,331 A | 12/1995 | Heflin et al. |
| 5,484,385 A | 1/1996 | Rishton |
| 5,505,701 A | 4/1996 | Anaya Fernandez de Lomana |
| 5,509,428 A | 4/1996 | Dunlop |
| 5,536,250 A | 7/1996 | Klein et al. |
| 5,558,617 A | 9/1996 | Heilman et al. |
| 5,569,296 A | 10/1996 | Marin et al. |
| 5,599,306 A | 2/1997 | Klein et al. |
| 5,609,628 A | 3/1997 | Keranen |
| 5,613,949 A | 3/1997 | Miraki |
| 5,613,980 A | 3/1997 | Chauhan |
| 5,617,878 A | 4/1997 | Taheri |
| 5,637,086 A | 6/1997 | Ferguson et al. |
| 5,643,171 A | 7/1997 | Bradshaw et al. |
| 5,643,215 A | 7/1997 | Fuhrman et al. |
| 5,669,924 A | 9/1997 | Shaknovich |
| 5,702,343 A | 12/1997 | Alferness |
| 5,713,853 A | 2/1998 | Clark et al. |
| 5,713,860 A | 2/1998 | Kaplan et al. |
| 5,720,735 A | 2/1998 | Dorros |
| 5,755,779 A | 5/1998 | Horiguchi |
| 5,762,599 A | 6/1998 | Sohn |
| 5,766,151 A | 6/1998 | Valley et al. |
| 5,776,190 A | 7/1998 | Jarvik |
| 5,797,876 A | 8/1998 | Spears et al. |
| 5,807,311 A | 9/1998 | Palestrant |
| 5,807,895 A | 9/1998 | Stratton et al. |
| 5,817,046 A | 10/1998 | Glickman |
| 5,820,585 A * | 10/1998 | Mobin-Uddin et al. ...... 604/508 |
| 5,902,229 A | 5/1999 | Tsitlik et al. |
| 5,902,336 A | 5/1999 | Mishkin |
| 5,913,852 A | 6/1999 | Magram |
| 5,928,132 A | 7/1999 | Leschinsky |
| 5,935,924 A | 8/1999 | Bunting et al. |
| 5,968,013 A | 10/1999 | Smith et al. |
| 5,971,910 A | 10/1999 | Tsitlik et al. |
| 5,984,955 A | 11/1999 | Wisselink |
| 6,001,079 A | 12/1999 | Pourchez |
| 6,013,054 A | 1/2000 | Jiun Yan |
| 6,039,721 A | 3/2000 | Johnson et al. |
| 6,068,629 A | 5/2000 | Haissaguerre et al. |
| 6,077,256 A | 6/2000 | Mann |
| 6,086,527 A | 7/2000 | Talpade |
| 6,086,557 A | 7/2000 | Morejohn et al. |
| 6,096,073 A | 8/2000 | Webster et al. |
| 6,117,117 A | 9/2000 | Mauch |
| 6,117,156 A | 9/2000 | Richter et al. |
| 6,142,973 A | 11/2000 | Carleton et al. |
| 6,143,002 A | 11/2000 | Vietmeier |
| 6,156,016 A | 12/2000 | Maginot |
| 6,165,120 A | 12/2000 | Schweich et al. |
| 6,190,349 B1 | 2/2001 | Ash et al. |
| 6,210,380 B1 | 4/2001 | Mauch |
| 6,251,133 B1 | 6/2001 | Richter et al. |

| | | |
|---|---|---|
| 6,261,273 B1 | 7/2001 | Ruiz |
| 6,261,316 B1 | 7/2001 | Shaolian et al. |
| 6,287,277 B1 | 9/2001 | Yan |
| 6,287,608 B1 | 9/2001 | Levin et al. |
| 6,325,826 B1 | 12/2001 | Vardi et al. |
| 6,383,172 B1 * | 5/2002 | Barbut ............... 604/509 |
| 6,387,037 B1 | 5/2002 | Bolling et al. |
| 6,390,969 B1 | 5/2002 | Bolling et al. |
| 6,468,241 B1 | 10/2002 | Gelfand et al. |
| 6,475,208 B2 | 11/2002 | Mauch |
| 6,482,211 B1 | 11/2002 | Choi |
| 6,494,875 B1 | 12/2002 | Mauch |
| 6,508,787 B2 | 1/2003 | Erbel et al. |
| 6,514,226 B1 | 2/2003 | Levin et al. |
| 6,533,747 B1 | 3/2003 | Polaschegg et al. |
| 6,540,779 B2 | 4/2003 | Richter et al. |
| 6,592,567 B1 | 7/2003 | Levin et al. |
| 6,595,959 B1 | 7/2003 | Stratienko et al. |
| 6,669,718 B2 | 12/2003 | Besselink |
| 6,699,231 B1 | 3/2004 | Sterman et al. |
| 6,733,474 B2 | 5/2004 | Kusleika |
| 6,749,598 B1 | 6/2004 | Keren et al. |
| 6,749,628 B1 | 6/2004 | Callol et al. |
| 6,884,258 B2 | 4/2005 | Vardi et al. |
| 6,887,258 B2 | 5/2005 | Denison et al. |
| 6,911,039 B2 | 6/2005 | Shiu et al. |
| 6,945,992 B2 | 9/2005 | Goodson et al. |
| 6,994,700 B2 | 2/2006 | Elkins et al. |
| 7,063,679 B2 | 6/2006 | Maguire et al. |
| 7,104,981 B2 | 9/2006 | Elkins et al. |
| 7,241,273 B2 | 7/2007 | Maguire et al. |
| 7,329,236 B2 | 2/2008 | Kesten et al. |
| 7,335,192 B2 | 2/2008 | Keren et al. |
| 7,341,570 B2 * | 3/2008 | Keren et al. ............ 604/96.01 |
| 7,364,566 B2 | 4/2008 | Elkins et al. |
| 7,381,204 B2 | 6/2008 | Wilson et al. |
| 7,470,252 B2 | 12/2008 | Mickley et al. |
| 7,563,247 B2 | 7/2009 | Maguire et al. |
| 7,585,836 B2 | 9/2009 | Goodson et al. |
| 2001/0023334 A1 * | 9/2001 | St. Goar et al. .......... 604/101.04 |
| 2001/0029349 A1 | 10/2001 | Leschinsky |
| 2001/0031907 A1 | 10/2001 | Downey et al. |
| 2002/0022857 A1 | 2/2002 | Goldsteen et al. |
| 2002/0090388 A1 | 7/2002 | Humes et al. |
| 2002/0091355 A1 | 7/2002 | Hayden |
| 2002/0091362 A1 * | 7/2002 | Maginot et al. ............ 604/264 |
| 2002/0165574 A1 | 11/2002 | Ressemann et al. |
| 2002/0169413 A1 | 11/2002 | Keren et al. |
| 2003/0050600 A1 | 3/2003 | Ressemann et al. |
| 2003/0069468 A1 | 4/2003 | Bolling et al. |
| 2003/0100919 A1 | 5/2003 | Hopkins et al. |
| 2003/0144636 A1 | 7/2003 | Liu |
| 2003/0153898 A1 | 8/2003 | Schon et al. |
| 2003/0181856 A1 | 9/2003 | Goldman |
| 2003/0220664 A1 | 11/2003 | Petrick et al. |
| 2004/0002730 A1 | 1/2004 | Denison et al. |
| 2004/0044302 A1 | 3/2004 | Bernard et al. |
| 2004/0064089 A1 | 4/2004 | Kesten et al. |
| 2004/0097900 A1 | 5/2004 | Keren et al. |
| 2004/0111148 A1 | 6/2004 | Goodson |
| 2004/0117003 A1 | 6/2004 | Ouriel et al. |
| 2004/0167415 A1 | 8/2004 | Gelfand et al. |
| 2004/0167463 A1 | 8/2004 | Zawacki et al. |
| 2004/0254236 A1 | 12/2004 | Dong et al. |
| 2005/0027305 A1 | 2/2005 | Shiu et al. |
| 2005/0197624 A1 | 9/2005 | Goodson et al. |
| 2005/0245882 A1 | 11/2005 | Elkins et al. |
| 2005/0245892 A1 | 11/2005 | Elkins et al. |
| 2005/0267010 A1 | 12/2005 | Goodson et al. |
| 2006/0030814 A1 | 2/2006 | Valencia et al. |
| 2006/0036218 A1 | 2/2006 | Goodson et al. |
| 2006/0047266 A1 | 3/2006 | Elkins et al. |
| 2006/0067972 A1 | 3/2006 | Kesten et al. |
| 2006/0069323 A1 | 3/2006 | Elkins et al. |
| 2006/0079836 A1 | 4/2006 | Holman et al. |
| 2006/0079859 A1 | 4/2006 | Elkins et al. |
| 2006/0149350 A1 | 7/2006 | Patel et al. |
| 2006/0167437 A1 | 7/2006 | Valencia |
| 2006/0259066 A1 | 11/2006 | Euteneuer |
| 2007/0053904 A1 | 3/2007 | Kirst et al. |
| 2007/0167913 A1 | 7/2007 | Elkins et al. |
| 2007/0213686 A1 | 9/2007 | Mathur et al. |
| 2007/0249997 A1 | 10/2007 | Goodson et al. |
| 2007/0287967 A1 | 12/2007 | Hekmat et al. |
| 2008/0103442 A1 | 5/2008 | Kesten et al. |
| 2008/0154236 A1 | 6/2008 | Elkins et al. |
| 2008/0221551 A1 | 9/2008 | Goodson et al. |
| 2009/0105799 A1 | 4/2009 | Hekmat et al. |
| 2009/0305990 A1 | 12/2009 | Goodson et al. |
| 2009/0306625 A1 | 12/2009 | Pereira et al. |
| 2009/0318857 A1 | 12/2009 | Goodson et al. |

FOREIGN PATENT DOCUMENTS

| | | |
|---|---|---|
| EP | 0 884 064 A2 | 12/1998 |
| EP | 1635736 | 3/2006 |
| EP | 1644070 | 4/2006 |
| EP | 1750506 | 2/2007 |
| EP | 1659970 | 5/2008 |
| EP | 1928535 | 6/2008 |
| EP | 1933920 | 6/2008 |
| EP | 1804879 | 12/2008 |
| EP | 2023997 | 2/2009 |
| GB | 2 239 675 A | 7/1997 |
| JP | 2006508776 | 3/2006 |
| JP | 2006526464 | 11/2006 |
| JP | 2006527629 | 12/2006 |
| JP | 2007521233 | 8/2007 |
| JP | 2007537298 | 12/2007 |
| JP | 2008514298 | 5/2008 |
| JP | 2009509644 | 3/2009 |
| JP | 2009511199 | 3/2009 |
| JP | 2009539504 | 11/2009 |
| WO | WO 97/11737 A1 | 4/1997 |
| WO | WO 98/03213 A1 | 1/1998 |
| WO | WO 98/17347 A1 | 4/1998 |
| WO | WO 98/52639 A1 | 11/1998 |
| WO | WO 99/22784 A1 | 5/1999 |
| WO | WO 99/33407 A1 | 7/1999 |
| WO | WO 99/51286 A1 | 10/1999 |
| WO | WO 00/41612 A1 | 7/2000 |
| WO | WO 01/37882 A | 5/2001 |
| WO | WO 01/41861 | 6/2001 |
| WO | WO 01/83016 A3 | 11/2001 |
| WO | WO 01/97687 A1 | 12/2001 |
| WO | WO 01/97717 A1 | 12/2001 |
| WO | WO 01/97878 A1 | 12/2001 |
| WO | WO 01/97879 A1 | 12/2001 |
| WO | WO 2004/26370 A | 4/2004 |
| WO | WO 2004/32791 A | 4/2004 |
| WO | WO 2004/030718 | 8/2004 |
| WO | WO 2005/002660 | 1/2005 |
| WO | WO 2005/014100 | 2/2005 |
| WO | WO 2004/107965 | 8/2005 |
| WO | WO 2005/091910 | 10/2005 |
| WO | WO 2005/112980 | 12/2005 |
| WO | WO 2006/036944 | 11/2006 |
| WO | WO 2007/041031 | 9/2007 |
| WO | WO 2007/044907 | 9/2007 |
| WO | WO 2007/146825 | 12/2007 |
| WO | WO 2008/112563 | 9/2008 |
| WO | WO 2009/055564 | 4/2009 |
| WO | WO 2009/114826 | 9/2009 |

OTHER PUBLICATIONS

Agostoni et al. "Sustained Benefit from Ultrafiltration in Moderate Congestive Heart Failure", *Cardiology* 2001:96 183-189.

Akaba et al., "A Cylinder-Shaped Balloon Catheter for the Management of Dissecting Aneurysms in Acute Stage," *Herz*, vol. 17, No. 6, pp. 390-393, Dec. 1992. Abstract Only.

Aspelin, et al., "Nephrotoxic Effects in High-Risk Patients Undergoing Angiography," *N Engl J Med*, Feb. 2003, vol. 348, No. 6, pp. 491-499.

Bakris et al., "Renal Hemodynamics in Radiocontrast Medium-Induced Renal Dysfunction: A Role for Dopamine-1 Receptors," *Kidney Internatinal*, vol. 56 pp. 206-210 (1999).

Beregi, et al., "Doppler Flow Wire Evaluation of Renal Blood Flow Reserve in Hyertenstive Patient With Normal Renal Arteries," *Cardio Vascular and Interventional Radiology*, vol. 23, pp. 340-346 (2000).
Bergey et al., "Transhepatic Insertion of Vascular Dialysis Catheters in Children: A Safe, Life-Prolonging Procedure," *Pediatr. Radiol.*, vol. 29, No. 1, pp. 42-50, Jan. 1999. Abstract Only.
Bischoff et al., "Modified in Situ Perfusion of the Kidney Using Balloon Catheters," *Fortschr Med* vol. 94, No. 30, pp. 1695-1697, Oct. 21, 1976. Abstract Only.
Chatterjee, "Refractory heart failure-drugs and devices", *European Heart Journal*, 2001, 22:2227-2230.
Chu, et al. "Fenoldopam in the Prevention of Contrast Media-Induced Acute Renal Failure," *The Annals of Pharmacotherapy*, 35:1278-1282 (2001).
Cohn, "The Management of Chronic Heart Failure," *The New England Journal of Medicine*, pp. 490-498, Aug. 15, 1996.
Darves, "ASHP: Perioperative Fenoldopam Improves Renal Function During Major Surgery," Retrieved from the Internet [Online]: www.pslgroup.com/dg/225C72.htm, Dec. 19, 2002.
Del Greco, "The Kidney in Congestive Heart Failure," *Modem Concepts of Cardiovascular Disease*, Sep. 1975, vol. 44, No. 9, pp. 47-52.
D'Elia et al., "Nephrotoxicity from Angiographic Contrast Material, A Prosepctive Study," *Am J Med*, May 1982, vol. 72, pp. 719-725.
Diaz-Sandoval, et al., "Acetylcysteine to Prevent Angiography-Related Renal Tissue Injury," *The American Journal of Cardiology*, Feb. 1, 2002: vol. 89, pp. 356-358.
Drescher et al., "Prevention of Contrast Medium-Induced Renal Vasospasm by Phosphodiesterase Inhibition," *Invest Radiol*, 1998;33:858-862.
Eisenberg et al., "Renal Failure after Major Angiography Can be Avoided with Hydration", *AJR*, May 1981; 136:859-861.
Eisenberg et al., "Renal Failure After Major Angiography," *Am J Med*, Jan. 1980, vol. 68, pp. 43-46.
Eisenberger et al., "Transfemoral Cannulation of the Renal Vessels. Diagnostic and Therapeutic use in Urology," *Urologe* [A], vol. 16, No. 1, pp. 1-5, Jan. 1977. Abstract Only.
Elkayam et al., "Renal Hemodynamic Effects of Vasodilation with Nifedipine and Hydralazine in Patients With Heart Failure," *JACC*, vol. 4, No. 6 (Dec. 1984), pp. 1261-1267.
Elkayam et al., "Renal Vasodilatory Effect of Endothelial Stimulation in Patients with Chronic Congestive Heart Failure," J Am Coll Cardiol 1996;28: 176-182.
Fox, "Mechanisms of Contraction," *Human Physiology*, Fourth Edition, Chapter 12, pp. 300-323.
Freeman, et al., "Nephropathy Requiring Dialysis After Percutaneous Coronary Intervention and the Critical role of an Adjusted Contrast Dose," *Am J Cardiol*, vol. 90, (Nov. 15, 2002) pp. 1068-1073.
Garwood et al., "Renal Preservation Strategies for High Risk Patients," *University of Chico School of Medicine*, Cover Page, Table of Contents Page, pp. 1-19, (1998).
Gerlach, et al., "Contrast Medium-Induced Nephrotoxicity: Pathophysiology and Prevention," *Pharmacotherapy*, 2000, 20(5):540-548.
Greco et al., "Atherosclerotic Ischemic Renal Disease," Am. J. Kidney Dis., vol. 29, No. 2, pp. 167-187, Feb. 1997. Abstract Only.
Gruberg, et al., "The Prognostic Implications of Further Renal Function Deterioration Within 48 h of Interventional Coronary in Patients With Pre-existent Chronic Renal Insufficiency," *J Am Coli Cardiol*, 2000, vol. 36 No. 5, pp. 1542-1548.
Halpenny, et al., "The effects of fenoldopam on fenal blood flow and tubular function during aortic cross-clamping in anaesthetized dogs," *Eur J Anaesthesia*, 2000 Aug.;17(8);491-8 Abstract Only.
Heyman et al.," Pathophysiology of Radiocontrast Nephropathy, A Role for Medullary Hypoxia," *Invest Radiol*, 1999;34:685-691.
Hobbs, et al., "An Update on Nesiritide for Treatment of Decompensated Heart Failure," Exp. Opin. Invest. Drugs, 2001, 10(5):935-942.
Houghton, et al., "Basal and Reserve Renal Artery Blood Flow: Effect of Endothelium-Dependent and Independent Vasoactive Agonists and Radiographcl Contrast Medium in Two Patients", *J invas Cardiol* 2000,12: 211-215.
Iannone at al., "Effect of Primary Balloon Expandable Renal Artery Stents on Long-Term Patency, Renal Function, and Blood Pressure in Hypertensive and Renal Insufficient Patients with Renal Artery Stenosis," *Cathet. Cardiovasc. Diagn.*, vol. 37, No. 3, pp. 243-250, Mar. 1996. Abstract Only.
Jacobs et al., "Reduced Renal Failure Following Thoracoabdominal Aortic Aneurysm Repair by Selective Perfusion," *Eur. J. Cardlothorac. Surg.*, vol. 14, No. 2, pp. 201-205, Aug. 1998. Abstract Only.
Katsumata et al., "Newly-Developed Catheter for Cardio-Renal Assist During Intraaortic Balloon Counterpulsation," *Kyobu Geka*, vol. 46, No. 9, pp. 767-770. Aug. 1993. Abstract Only.
Kay, et al., Acetylcysteine for Prevention of Acute Deterioration of Renal Function Following Elective Coronary Angiography and Intervention, *JAMA*, vol. 289 No. 5, (Feb. 5, 2003).
Kehrer et al., "Construction and Experimental Application of a Catheter for Selective Arterial Kidney Perfusion in Situ", *Urological Research*, 1985, 13:85-89.
Kim at al., "Fluoroscopic Landmarks for Optimal Visualization of the Proximal Renal Arteries," *JVIR*, 10:37-39 (1999).
Kini et al., "A Protocol for Prevention of Radiographic Contrast Nephropathy During Pecutanous Coronary Intervention," *Catheterization and Cardiovascular Interventions*, 2002, 55:169-173.
Kini, et al., "Managing the High-Risk Patient: Experience with Fenoldopam, a Selective Dopamine Receptor Agonist in Prevention of Radiocontrast Nephropathy During Precutaneous Coronary Intervention," *Rev Cardiovasc Med. 2001*, 2(suppl 1):S19-S25.
Kobayashi et al., "Experimental Study on the Usefulness of the Autoperfusion Balloon Catheter in Maintaining the Blood Supply to the Distal Organs," *Nippon Igaku Hoshasen Gakkai Zasshi*, vol. 52, No. 5, pp. 682-684, May 25, 1992. Abstract Only.
Lass et al., "Cardiovascular and Renal Hemodynamic Effects of Intravenous Infusions of the Selective $DA_1$ Agonist, Fenoldopam, Used Alone or in Combination With Dopamine and Dobutamine", *Circulation* 1988;78;1310-1315.
Levin, Howard et al., "Reversal of Chronic Ventricular Dilation in Patients with End-Stage Cardiomyopathy by Prolonged Mechanical Unloading," *Circulation* vol. 91, No. 11, pp. 2717-2718, Jun. 1, 1995.
Linden et al., "The Nature of the Atrial Receptors Responsible for a Reflex Decrease in Activity in Renal Nerves in the Dog," *The Physiological Society*, pp. 31-40, (1980).
Madyoon, "Clinical Experience with the Use of Fenoldopam for Prevention of Radiocontrast Hephropathy etc," *Rev Cardiovasc Med.* 2001, 2(suppl 1 );S26-S30.
Madyoon, "Use of Fenoldopam to Prevent Radiocontrast Nephropathy in High-Risk Patients," *Catheterization and Cardiovascular Interventions*, 2001;53:341-345.
Margulies at al., "Intra-Arterial Atrial Natriuretic Factor (ANF) Attenuates Radiocontrast-Induced Nephropathy in Humans.," *Renal Pathology*, unknown date, pp. 666, Abstract only.
Margulies at al.," Induction and Prevention of Radiocontrast-induced Nephropathy in Dogs with Heart Failure", *Kidney Int*. 1990; vol. 38:1101-1108.
Masaki at al., "In Situ Perfusion by Retrograde Cannulation of a Tumor Artery Nephron-Sparing Surgery," *Int. J. Urol*, vol. 2, No. 3, pp. 161-165. Jul. 1995. Abstract Only.
Mason at al., "Renal Dysfunction After Arteriography," *JAMA*, 1985;253:1001-1004.
Mathis et al., "Use of a Guide Catheter as a Temporary Stent During, Microcatheter Intervention," *AJNR Am. J. Neuroradiol*, vol. 19 No. 5, pp. 932-933. May, 1998. Abstract Only.
Mathur, "The Role of the $DA_1$ Receptor Agonist Fenoldopam in the Management of Critically Ill, Transplant, and Hypertensive Patients," *Reviews in Cardiovascular Medicine*, 2003;4(Supp 1):S35-S40.
Mathur, et al., "The Effects of Fenoldopam, a Selective Dopamine Receptor Agonist, on Renal Hemodynamics in Normotensive Subjects," *Crit Cre Med* Sep. 1999;27(9):1832-1837, Abstract only.
McCarthy, "Animal Models in Medical Device Development and Qualification," *Charles River Laboratories*, vol. 10(2)1997.
McCullough et al., "Acute Renal Failure After Coronary Intervention: Incidence, Risk Factors, and Relationship to Mortality," *Am J Med*. 1997;103:368-375.

Mehran, et al., "A Risk Score for Prediction of Contrast Induced Nephropathy After Percutaneous Coronary Intervention," Retrieved from the Internet [Online]: www.abstractsonline.com/viewer, Mar. 31, 2003.
Mehran, et al., "Radiocontrast-Induced Acute Renal Failure: Allocations and Outcomes," *Rev Cardiovasc Med* 2001;2(suppl1):S9-S13.
Middleton, "Ischemic Disease of the Kidney: How and Why to Consider Revascularization," *J. Nephrol.*, vol. 11, No. 3, pp. 123-136, May-Jun. 1998. Abstract Only.
Miller, at al., "Effects of Fenoldopam on Renal Blood Flow and Tubular Function Following Supraerenal Aortic Cross-Clamping," *Ann Vasc Surg*, 2003, Published online Oct. 23, 2003. Abstract Only.
Mintz, et al., "Radiocontrast-Induced Nephropathy and Percutaneous Coronary Intervention," *Expert Opin. Pharmacother.*, 2003; 4(5):639-652.
Mueller, et al., "Prevention of Contrast Media-Associated Nephropathy," *Arch Intern med*, Feb. 2002, vol. 162, pp. 329-336.
Nohria, et al., Medical Management of Advanced Heart Failure, JAMA, Feb. 6, 2002; vol. 287, No. 5, pp. 628-640.
Novick, "Atherosclerotic Ischemic Nephropathy. Epidemiology and Clinical Considerations," *Urol. Clin. North Am.*, vol. 21, No. 2, pp. 195-200, May 1994. Abstract Only.
Paganini, et al., "Severity Scores and Outcomes With Acute Renal Failure in the ICU Setting," *Contrib Nephrol*, 2001; 132: 181-195.
Parfrey at al., "Contrast Material-Induced Renal Failure in Patients with Diabetes Mellitus, Renal Insufficiency, or Both," *N Engl J Med* 1989; 320:143-149.
Patel at al., "Intravenous Fenoldopam Infusion in Severe Heart Failure," *Cardiovasc Drugs Ther* , 1993;7:97-101.
Postma et al., "Treatment of Renal Artery Stenosis with Intra-Arterial Stents," *Ned Tijdschr Geneeskd*, vol. 142, No. 39. pp. 2132-2137, Sep. 26, 1998. Abstract Only.
Ramanathan, et al., "Ameliorating Contrast-Induced Nephropathy", Journal of Invasive Cardiology, Nov. 2001, Retrieved from the Internet [Online]: www.invasivecardiology.comlfic_2001/jic_200111f6.html.
Rebeiz, et al., "Radiocontrast Nephropathy: a Time for Affirmative Action, *J Invasive Cardiology*," Jan. 2003; vol. 15, No. 1, pp. 23-24.
Rihal, et al., "Incidence and Prognostic Importance of Acute Renal Failure After Percutaneous Coronary Intervention," *Circulation*, (May 14, 2002),105:2259-2264
Ritchie, et al., "Use of nonionic or Low Osmolar Contrast Agents in Cardiovascular Procedures," Retrieved from the Internet [Online] www.acc.org/clinlcal/position/72543.htm, Jan. 22, 2003
Robinson, at al., "Congestive Heart Failure: Targeted Drug Therapy and Invasive Interventions", Retrieved from the Internet [Online] www.speroff.com/articieslTextbook/66_CHF2.htm, printed Sep. 4, 2002.
Rudnick at al., "Nephrotoxicity of Ionic and Noionic Contrast Media in 1196 Patients: A Randomized Trial," *Kidney International*, 1995;47:254-261.
Schwab et al., "Contrast Nephrotoxicity: A Randomized Controlled Trial of a Nonionic and an Ionic Radiographic Contrast Agent," *N Engl J Med*, 1989,320:149-153.
Seiter, H. et al., "Modified T-Catheter and its Use for Transvenous Hypothermic in Situ Perfusion in the Surgical Restoration of the Kidney with Staghom Calculi," *Z. Urol Nephrol.*, vol. 76 No. 6 pp. 403-406, Jun. 1983. Abstact Only.
Shusterman et al., "Fenoldopam, But Not Nitroprusside, Improves Renal Function in Severely Hypertensive Patients With Impaired Renal Funcion," *Am J of Medicine*, 95:161-168 (1993).
Solomon et al., "Effects of Saline, Mannitol, and Furosemide on Accute Decreases in Renal Function Induced by Radiocontrast Agents.," *N Engl J Med* 1994; vol. 331 No. 21 pp. 1416-1420.

Stevens et al., "A Prospective Randomized Trial of Prevention Measures in Patients at High Risk for Contrast Nephropathy," *J Am Coli Cardiol*, 1999;33:403-411.
Strick et al., "Direct Measurement of Renal Medullary Blood Flow in the Dog," *Am J. Physiol.* 267 (Regulatory Integrative Compo Physiol. 36): R253-R2259, 1994.
Suehiro, et al., "Selective Renal Vasodilation and Active Renal Artery Perfusion Improve Renal Function in Dogs with Acute Heart Failure," *The Journal of Pharmacology and Experimental Therapeutics*, vol. 298. No. 3 pp. 1154-1160 (2001).
Taliercio et al., "Risks for Renal Dysfunction with Cardiac Angiography," *Annals of Internal Medicine*, 1986;104:501-504.
Thomas et al., "Glomerrular Filtration Dynamics During Renal Vasodilation with Acetylcholine in the Dog.," *Am. J. Physic.* 244:F606-F611 (1983).
Thomas et al., "Influence of Bradykinin and Papaverine on Renal and Glomerular Hemodynamics in Dogs.," *Renal Physiology*, Basel 5:197-205 (1982).
UIC College of Pharmacy, "Is Fenoidoparn (Corlopam) Useful for the Prevention of Contrast Media Associated Nephrotoxicity?", Retrieved from the Internet [Online] www.uic.edu/pharmacy/services/di/fenoldopam.htm, Jan. 2003.
Umrani, et al., "Beneficial Effects Offenoldopam Treatment on Renal Function in Streptozotcin-Induced Diabetic Rats," *Clin Exp Hypertens*, Apr. 2002;24(3):207-19 Abstract Only.
Vari et al., "Induction, Prevention and Mechanisms of Contrast Media-Induced Acute Renal Failure," *Kidney International*, 1988; 33:669-707.
Walker et al., "Use of a Balloon-Tipped Perfusion Catheter for Renal Preservation During Suprarenal Abdominal Aortic Operations," *J. Vasc. Surg.*, vol. 2, No. 2, pp. 337-339, Mar. 1985. Abstract Only.
White et al., "Renal Artery Stent Placement: Utility in Lesions Difficult to Treat with Balloon Angioplasty," *J. Am. Coll. Cardiol.*, vol. 30, No. 6, pp. 1445-1450, Nov. 15, 1997. Abstract Only.
Williams et al., "Design and Testing of a High-FLO2 Autoperfusion Catheter: An Experimental Study," *J. Vasc. Interv. Radiol.*, vol. 3. No. 2, pp. 285-290. May, 1992. Abstract Only.
Zacherl, et al. "Periarterial Papaverine Applications Improves Intraoperative Kidney Function During Laparoscopic Donor Nephrectomy", *Journal of Surgical Research* 103:268-271 (2002).
Maydoon, Hooman et al., Fenoldopam for prevention of contrast-induced renal dysfunction in a high risk angiography population: A historically-controlled case series:, Circulation, vol. 104, No. Suppl 17, Oct. 23, 2001, p. II.185, XP009098219.
Stone, G.W. et al., "Designand rational of Contrast—a prospective, randomized, placebo-controlled trial of fenoldopam mesylate for the prevention of radiocontrast nephropathy", Reviews in Cardiovascular Medicine, vol. 2, No. Suppl.1, 2001, pp. 531-536, XP009098217.
Thatipelli et al., "CT Angiography of Renal Artery Anatomy for Evaluting Embolic Protection Devices." Journal of Vascular and Interventional Radiology. 2007: 18(7):842-846.
Tumlin et al., "A multicenter, double-blind, placebo-controlled trial of fenoldopam meysylate in the prevention of radiocontrast nephropathy in patients with moderate to severe renal insufficiency" Journal of the American Society of Nephrology, Vo. 11, Sep. 2000, p. 135A, XP009098223.
Van Der Zander et al., "Hypertension: Does Brain Natriuretic Paptide Have a Direct Renal Effect in Human Hypertensives?", American Heart Association, 2003, 41, 119-123.
Venkatamaran, "Prevention of acute renal failure," Crit. Care Clin., 2005, 21(2), 281-289 (abstract).
Weisberg et al., Risk of radiocontrast nephropathy in patients with and without diabetes mellutus, Kidney International, 1994, 45:259-265.

* cited by examiner

SHEATH FOR USE IN PERIPHERAL INTERVENTIONS

CROSS-REFERENCES TO RELATED APPLICATIONS

The present application is a divisional of U.S. patent application Ser. No. 11/073,421, entitled "Sheath for use in peripheral interventions", filed Mar. 4, 2005 and claims priority to U.S. Provisional Patent Application Nos. 60/550,632, filed Mar. 4, 2004, and 60/550,774, , filed Mar. 5, 2004, the full disclosures of which are hereby incorporated by reference.

BACKGROUND OF THE INVENTION

The present invention is related to medical devices, methods and systems. More specifically, the invention is related to devices, methods and systems for accessing various blood vessels in a patient, such as one or both renal arteries and one or more peripheral vessels.

In the setting of interventional radiology, numerous conditions exist that warrant placement of various intravascular devices into the lower limb arteries (iliac, femoral, popliteal, etc.). Such devices may include catheters and guidewires for diagnostic purposes, or systems for therapeutic or prophylactic applications such as drug infusion, monitoring/sampling, angioplasty and stenting, possibly in conjunction with embolic protection. In any event, these procedures often involve the use of radiocontrast agents known to have detrimental effects on renal function.

In many instances, lower limb arteries intended for diagnosis or intervention are accessed via an "up-and-over" approach, which first involves gaining arterial access on one side of the patient, typically though not necessarily via a femoral artery. From that access point, one or more diagnostic, prophylactic, and/or treatment devices are advanced in a retrograde fashion through the iliac artery on the side of access to the aortic bifurcation and then down along the direction of blood flow on the contralateral side, through the contralateral iliac artery, into and possibly through the contralateral femoral artery, etc. to the site of treatment and/or diagnostic procedure. As mentioned above, performing the treatment and/or diagnostic procedure often involves injection of a radiocontrast agent to allow the physician(s) to visualize the treatment/diagnostic site.

The nephrotoxicity of radio contrast agents has been well established. In patients with known risk factors, radiocontrast nephropathy (RCN) is a prevalent adverse effect of interventional procedures utilizing organically bound iodine-based contrast imaging agents. While the full mechanism of RCN is not known, its detrimental results on morbidity and mortality are well documented, and it is hypothesized that local agent administration to the renal arteries during the time of contrast media exposure may mitigate the development of RCN. Agents in this case may include vasodilators, diuretics, or hyper-oxygenated blood or blood substitute. As well as agent infusion, the exchange of blood laden with contrast media and replacement of it with filtered blood, via use of an external blood filter/pump might be warranted.

Various apparatus and methods for providing local delivery of substances to renal arteries have be described by the inventors of the present invention in U.S. patent application Ser. No. 09/724,691, filed Nov. 28, 2000; Ser. No. 10/422,624, filed Apr. 23, 2003; Ser. No. 10/251,915, filed Sep. 20, 2002; Ser. No. 10/636,359, filed Aug. 6, 2003; and Ser. No. 10/636,801, filed Aug. 6, 2003, the full disclosures of which are all incorporated herein by reference. Apparatus and methods for renal delivery of substances have also been described in PCT Patent Application Nos.: PCT/US03/029744, filed Sep. 22, 2003; PCT/US03/29995, filed Sep. 22, 2003; PCT/US03/29743, filed Sep. 22, 2003; and PCTIUS03129585, filed Sep. 22, 2003, the full disclosures of which are all incorporated herein by reference.

For the reasons described above, in some diagnostic and treatment procedures performed in the peripheral vasculature, especially in patients with renal risk factors, it may be desirable to concurrently provide for a means of renal protection via site-specific agent delivery to the renal arteries. Thus, a need exists for devices, methods and systems that provide access to one or more renal arteries and to one or more peripheral vessels. Ideally, such devices, methods and systems would allow for access and substance delivery through a common introducer device that provides access via a femoral artery. At least some of these objectives will be met by the present invention.

BRIEF SUMMARY OF THE INVENTION

In one aspect of the present invention, a single lumen introducer sheath for accessing at least one renal artery and at least one peripheral blood vessel of a patient includes a proximal hub comprising first and second ports and a lumen extending from the ports and having proximal and distal apertures. The lumen extends from the first and second ports and has sufficient length such that when the ports are positioned outside the patient a distal end of the lumen is positionable in the abdominal aorta at or near origins of the patient's renal arteries. The proximal aperture in the lumen is configured to allow passage of a vascular catheter device through the proximal aperture and into or through an iliac artery contralateral to an insertion point of the introducer sheath into the patient. The distal aperture at the distal end of the lumen is configured to allow passage of a bifurcated renal catheter device out of the distal aperture to enter at least one of the renal arteries. Typically, though not necessarily, the proximal aperture comprises a side aperture in the lumen.

For purposes of the present application, the term "contralateral" refers to the side of the patient that is opposite the side in which an introducer sheath is placed. Various embodiments of the sheath described herein may be placed on either side of a patient, typically though not necessarily via a femoral artery access site. Thus, in one example where a sheath is inserted into a patient's right femoral artery, then the left side of the patient's body would be the contralateral side. If a sheath is inserted into a patient's left femoral artery, then the contralateral side is the right side.

In another aspect of the present invention, a dual lumen introducer sheath for accessing at least one renal artery and at least one peripheral blood vessel of a patient includes a proximal hub comprising first and second ports, a first lumen, and a second lumen. The first lumen extends from the first port to a first distal aperture and has sufficient length such that when the first port is positioned outside the patient the first distal aperture is positionable in the abdominal aorta at or near origins of the patient's renal arteries. The second lumen extends from the second port to a second distal aperture and has a shorter length than the length of the first lumen. The second lumen is configured to allow passage of a catheter device through the second lumen and into or through an iliac artery contralateral to an insertion point of the introducer sheath into the patient.

In some embodiments, the first and second lumens are disposed side-by-side in a proximal portion of the introducer sheath, and the first lumen extends beyond the proximal portion. In some embodiments, the first lumen is configured to accept a bifurcated catheter for delivering one or more substances into the renal arteries. The second lumen may be configured to accept, for example, a balloon angioplasty catheter device for performing an angioplasty procedure in one or more peripheral arteries.

In another aspect of the present invention, a method for advancing at least two catheter devices into vasculature of a patient first involves positioning a single lumen introducer sheath in the patient such that the sheath extends from a proximal, two-port hub outside the patient into one of the patient's iliac arteries, and thus to a distal end in an abdominal aorta at or near origins of renal arteries of the patient. Next, a bifurcated renal artery catheter device is advanced through the distal end of the sheath's lumen to extend into the renal arteries, and a vascular catheter device is advanced through a proximal aperture in the lumen into at least one peripheral vessel of the patient on a contralateral side of the patient relative to an insertion point of the sheath. In various embodiments, the vascular catheter may be advanced through the introducer sheath before or after the renal catheter is advanced.

In some embodiments, the method further involves delivering at least one substance into at least one of the renal arteries through the bifurcated renal artery catheter device. For example, substances which may be delivered through the renal artery catheter device include, but are not limited to, vasodilators, diuretics, hyper-oxygenated blood, hyper-oxygenated blood substitutes and filtered blood. In some embodiments, the method further involves delivering at least one additional substance into peripheral vessel(s) of the patient through the vascular catheter device. For example, such an additional substance may include, but is not limited to, a radio contrast agent. Optionally, the method may further include performing an interventional procedure in at least one peripheral vessel of the patient, using the vascular catheter device. One example of such a procedure is an angioplasty procedure.

In another aspect of the present invention, a method for advancing at least two catheter devices into vasculature of a patient involves positioning a dual lumen introducer sheath in the patient such that the sheath extends from a proximal hub outside the patient into one of the patient's iliac arteries, and thus to a first distal aperture of a first lumen in the abdominal aorta at or near origins of renal arteries of the patient and to a second distal aperture of a second lumen in or near the iliac artery in which the sheath is positioned. The method then involves advancing a bifurcated renal artery catheter device through the first lumen and first distal aperture to extend into the renal arteries. The method then involves advancing a vascular catheter device through the second lumen and second distal aperture into at least one peripheral vessel of the patient on a contralateral side of the patient relative to an insertion point of the sheath. Again, in various embodiments, the vascular catheter may be advanced through the sheath either before or after the renal catheter is advanced.

In another aspect of the invention, a system for accessing at least one renal artery and at least one peripheral blood vessel of a patient includes a single lumen introducer sheath, a bifurcated renal artery catheter device for advancing through the first lumen to access the renal arteries, and a vascular catheter device for advancing through the second lumen and into or through the contralateral iliac artery. The single lumen sheath includes a proximal hub, a lumen, a proximal aperture in the lumen, and a distal aperture at the distal end of the lumen, as described above. The sheath may include any of the features previously described.

In some embodiments, the bifurcated renal artery catheter device is configured to expand from a constrained configuration within the introducer sheath to a deployed configuration in which two oppositely directed distal ends are positioned within the two renal arteries of the patient. In some embodiments, one of the two distal ends includes an aperture for allowing passage of fluid from the bifurcated renal artery catheter into one of the renal arteries. In alternative embodiments, each of the two distal ends includes an aperture for allowing passage of fluid from the bifurcated renal artery catheter into one of the renal arteries. The vascular catheter may comprise any diagnostic and/or treatment catheter device suitable for accessing and performing a function in a blood vessel. In one embodiment, for example, the vascular catheter device comprises a balloon angioplasty catheter.

In another aspect of the present invention, a system for accessing at least one renal artery and at least one peripheral blood vessel of a patient includes a dual lumen introducer sheath, a bifurcated renal artery catheter device for advancing through the first lumen to access the renal arteries, and a vascular catheter device for advancing through the second lumen and into or through the contralateral iliac artery. The dual lumen introducer sheath includes a proximal hub, a first lumen, and a second lumen, as described above. The introducer sheath may include any of the features previously described.

These and other aspects and embodiments of the invention will be described in further detail below, with reference to the attached drawing figures.

BRIEF DESCRIPTION OF THE DRAWINGS

FIGS. 2A and 2B are end-on cross-sectional views of the dual lumen sheath of FIG. 2, at different points along the length of the sheath.

FIG. 2C is an end-on cross-sectional view of a dual lumen sheath, according to an alternative embodiment of the present invention.

DETAILED DESCRIPTION

Figure 1:
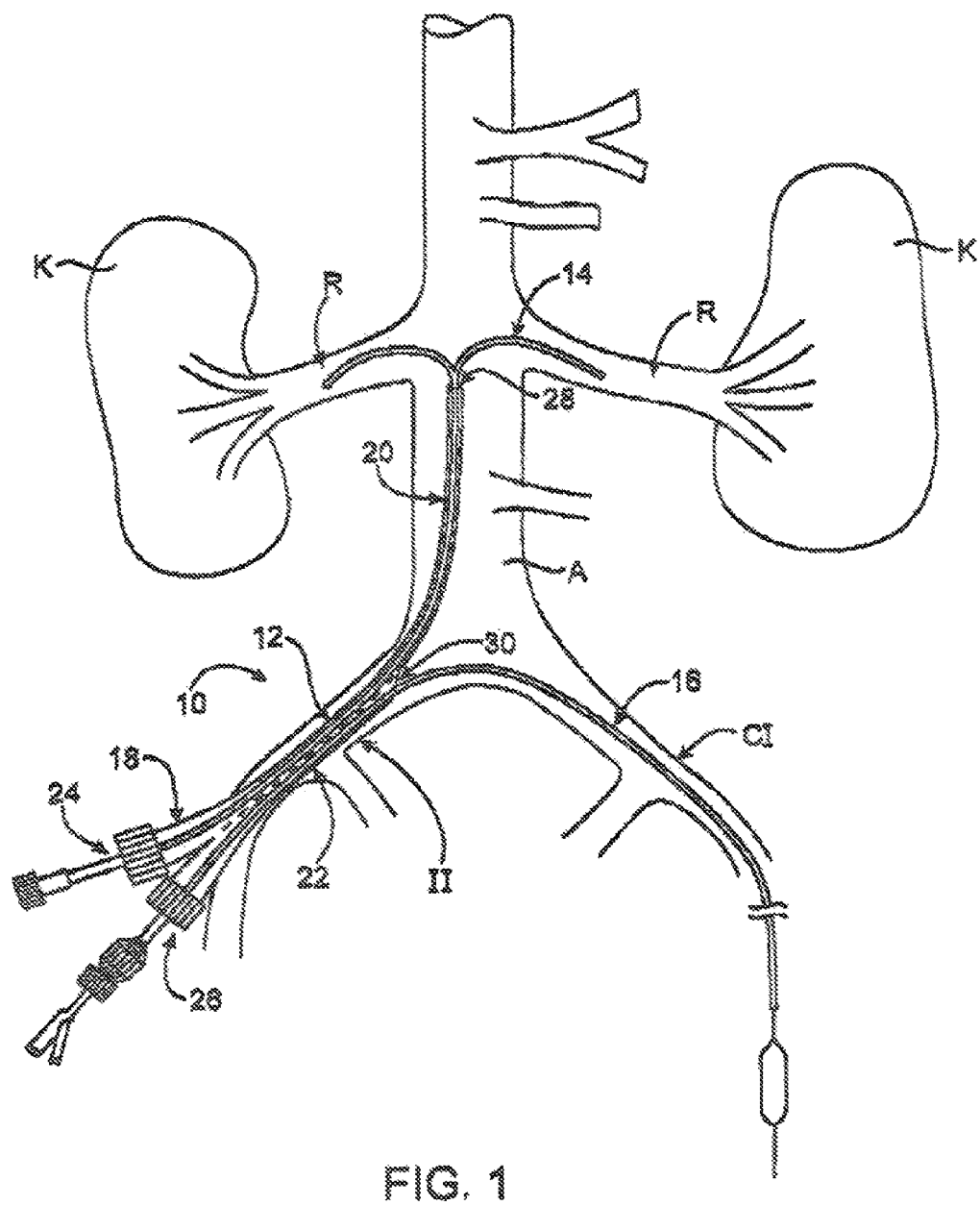
FIG. 1 is a side view of a dual lumen sheath and catheter system for accessing renal arteries and peripheral vessels, shown in situ, according to one embodiment of the present invention.

Referring to FIG. 1, a vascular access system in one embodiment suitably includes a dual lumen introducer sheath 12, a bifurcated renal catheter 14 and an additional vascular catheter device 16. As will be described in further detail below, in alternative embodiments, introducer sheath 12 may have only one lumen, with distal and proximal apertures. In the embodiment shown in FIG. 1, introducer sheath 12 includes a proximal hub 18 having first and second ports 24, 26, a first lumen 20 in fluid communication with first port 24 and a first distal aperture 28, and a second lumen 22 in fluid communication with second port 26 and a second distal aperture 30. Introducer sheath 12 is typically, though not necessarily, introduced into a patient through a femoral artery and advanced into an iliac artery, which in FIG. 1 is referred to as the ipsilateral iliac artery II. Upon positioning of sheath 12, first lumen 20 extends into the patient's aorta A such that first distal aperture 28 locates at or near the origins of the patient's renal arteries R, which lead from the aorta A to the kidneys K. Meanwhile, second lumen 22 ends more proximally in second distal aperture 30, which upon positioning of sheath 12 typically resides in or near the ipsilateral iliac artery II.

Introducer sheath 12 is generally adapted to be placed at the desired in-vivo location via traditional vascular access technique. After this placement, bifurcated renal artery catheter 14 is delivered into first entry port 24 on hub 18 and advanced through first lumen 20 to extend out first distal aperture 28, such that each of its two branches is positioned within a renal artery R. In various embodiments, bifurcated renal artery catheter 14 may be any of a number of suitable renal catheter devices, many examples of which are described in the patent applications incorporated by reference above in the background section. In some embodiments, bifurcated catheter 14 may be adapted to access both renal arteries, while in alternative embodiments only one renal artery may be accessed, and the opposite arm of the bifurcated catheter may act as an anchor or support. Once it is placed in a desired position, bifurcated renal artery catheter 14 may be used to selectively infuse one or more agents, typically renal protective agents, into the renal arteries. Such agents may include, but are not limited to, vasodilators, saline, diuretics, hyper-oxygenated blood, hyper-oxygenated blood substitutes and filtered blood. In other embodiments, other agent(s) may be used prevent or reduce negative effects of one or more radiocontrast agents that are subsequently or simultaneously delivered elsewhere. In some embodiments, system 10 may include a source of such agent(s).

In some embodiments, once renal catheter 14 is positioned, vascular catheter device 16 may then be advanced into second entry port 26 on hub 18, advanced through second lumen 22 and second distal aperture 30, and further advanced into and possibly through the contralateral iliac artery Cl. Depending on the desired treatment and/or diagnosis site, vascular catheter 16 may be advanced into the contralateral femoral artery or through the contralateral femoral artery into one or more peripheral vessels. Vascular catheter device 16 itself may comprise any of a number of suitable devices, such as a balloon angioplasty catheter (as shown), an atherectomy catheter, an ultrasound catheter, an infusion catheter or the like. Once placed in a desired position in the contralateral peripheral vasculature of the patient, vascular catheter 16 may then be used to perform one or more diagnostic and/or therapeutic procedures. Many of such procedures involve the introduction of one or more radiocontrast dyes or agents, and any adverse effects of such agents on the kidneys K will be mitigated by the substance(s) delivered via bifurcated renal artery catheter 14.

In various embodiments, system 10 may include additional, fewer and/or alternative components or devices. Furthermore, in various embodiments of a method for using system 10, the various steps may be performed in a different order and/or steps may be added or eliminated. For example, in one embodiment, a renal protective substance may be delivered via renal catheter 14 at the same time that a radiocontrast agent is delivered via vascular catheter 16. In another embodiment, the method may involve multiple infusions of renal protective substance(s) and/or multiple infusions of radio contrast material(s) in any of a number of different orders. Thus, the described method is but one preferred way in which vascular access system 10 may be used.

Figure 2:
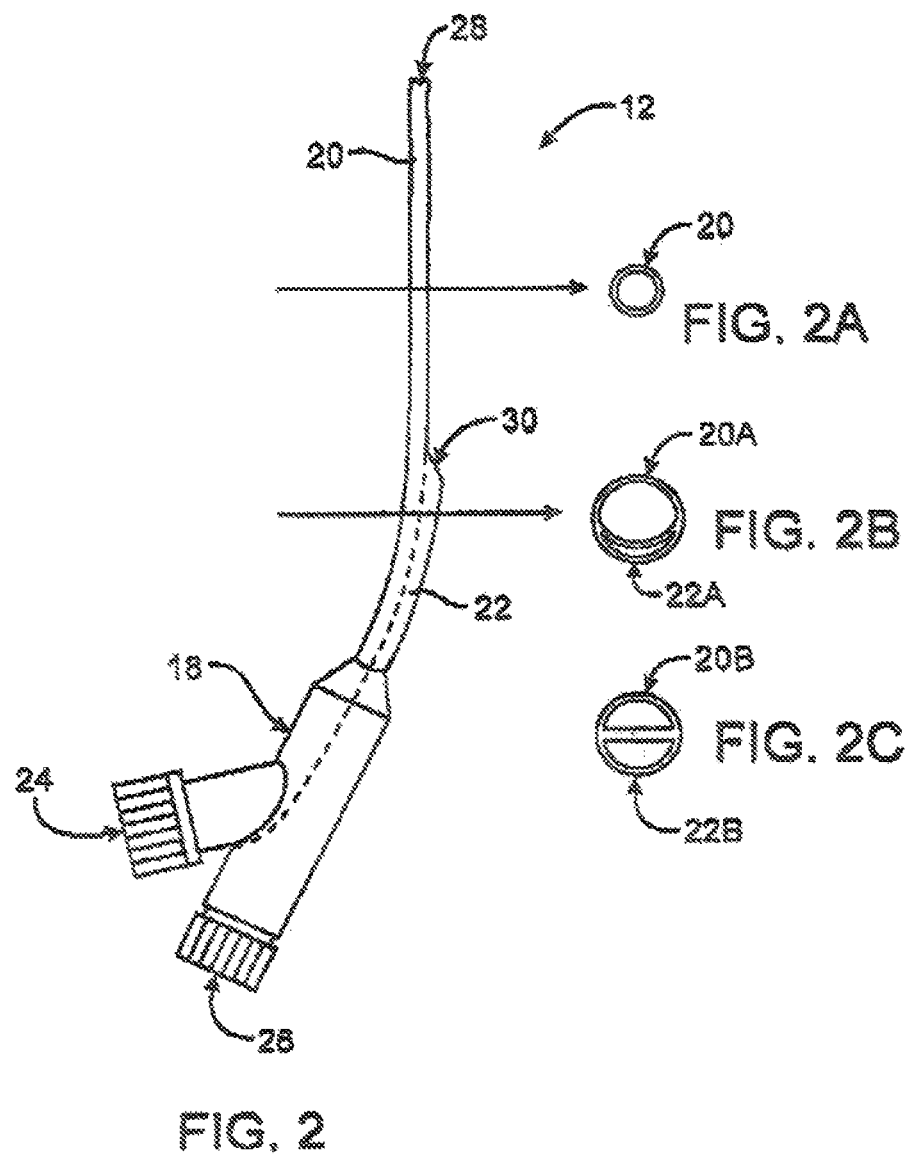
FIG. 2 is a side view of a dual lumen sheath for providing access to renal arteries and peripheral vessels, according to one embodiment of the present invention.

With reference now to FIG. 2-2C, dual lumen introducer sheath 12 is shown in greater detail. Again, sheath includes Y-shaped proximal hub 18, which allows for introduction of multiple (in the exemplary case two) devices simultaneously. In some embodiments, hub 18, first lumen 20 and second lumen 22 may each be sized to allow passage of devices up to about 10 French in outer diameter, or possibly even more, with a preferred embodiment being compatible with a renal catheter via first lumen 20 and a 5 Fr. to 8 Fr. peripheral diagnostic or interventional catheter via second lumen 22. FIG. 2A shows a cross-section of first lumen 20, FIG. 2B shows a cross-section of first and second lumens 20, 22, in a more proximal portion of sheath 12, and FIG. 2C shows a cross-section of an alternative embodiment of the more proximal portion, with a different design of first and second lumens 20, 22. The overall usable length of sheath 12 is generally such that it allows for standard femoral access (or other access point), and also allows first distal aperture 28 in first lumen 20 to reach a location at or near the renal arteries in order to deliver the bifurcated renal catheter. Again, various lengths for this device may also be provided to suit individual patients' anatomies, such as in a kit that allows for a particular device to be chosen for a particular case. Should an independently collapsible and expandable renal catheter be employed, the sheath's overall length may be reduced as desired.

Because sheath 12 maybe delivered to the peri-renal aorta, past the aortic bifurcation, sheath 12 may be further adapted to allow for the diagnostic or interventional device performing the lower limb procedure to exit along its length at a pre-determined or variable location so as to allow for the "up-and-over" delivery about the aortic bifurcation as previously discussed. In one particular embodiment, this may involve an aperture or other opening in the side wall of sheath 12 at an appropriate point. In an alternative embodiment, as shown in FIGS. 1-2C and as described above, a dual-lumen design may be adapted to deliver one device to the peri-renal aorta and the other to the area of the bifurcation. In a further embodiment, a valve apparatus (or multiple apparatuses) in combination with one or both of the other designs may be employed. In any event, sheath 12 may provide a mechanism for delivering one device (such as for example the renal catheter) to the level of the peri-renal aorta while simultaneously or contemporaneously allowing for another device (such as for example the peripheral diagnostic or interventional device) to exit lower at the area of the bifurcation. In the case of an independently collapsible and expandable renal catheter, a shorter sheath may be used that reaches just to or below to the level on the aortic bifurcation (i.e., still in the iliac artery on the side of access). Both devices may be simultaneously or contemporaneously deployed to their respective sites.

Figure 3:
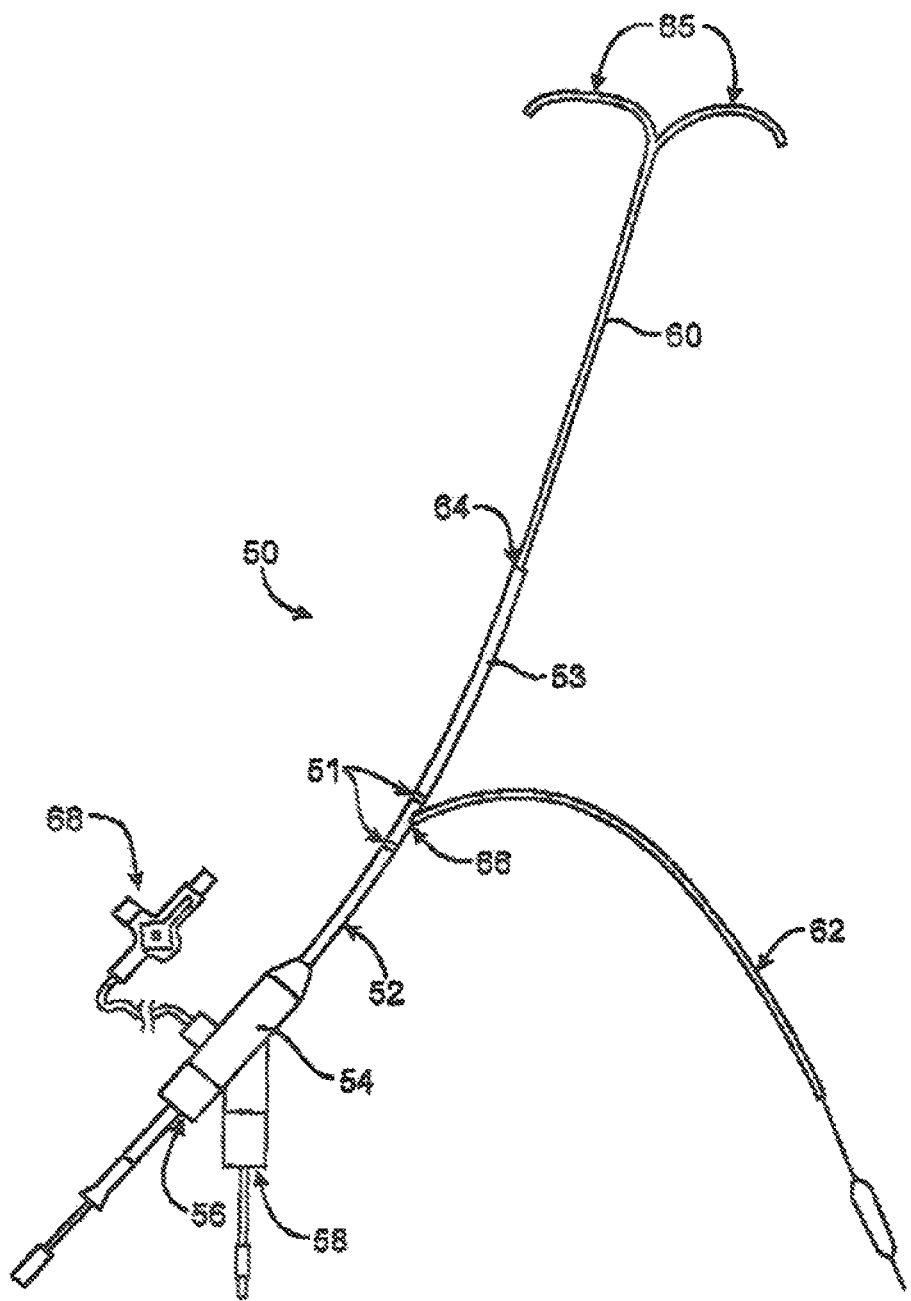
FIG. 3 is a side view of a single lumen sheath and catheter system for accessing renal arteries and peripheral vessels, according to an alternative embodiment of the present invention.
Figure 4:
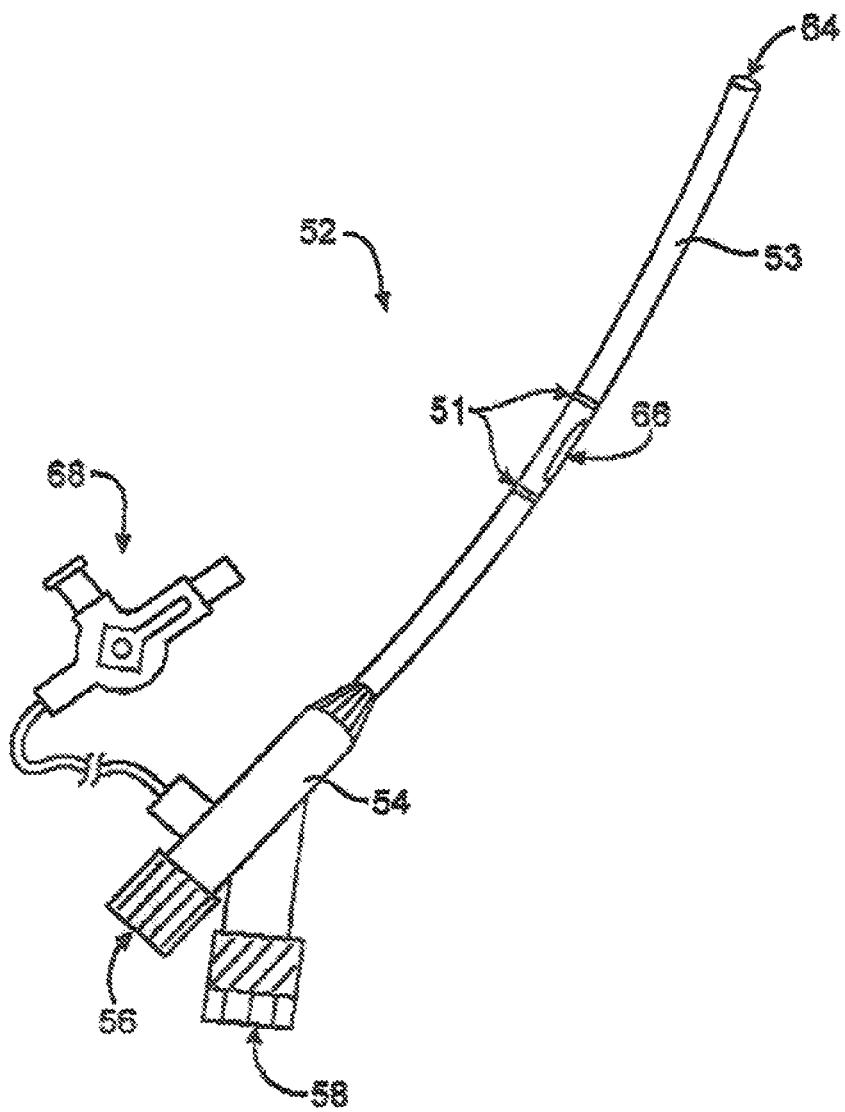
FIG. 4 is a side view of the single lumen sheath of FIG. 3.

Referring now to FIGS. 3 and 4, an alternative embodiment of a vascular access system 50 and a single lumen introducer sheath 52 are shown. In FIG. 3, vascular access system includes single lumen introducer sheath 52, a bifurcated renal catheter 60 and a vascular catheter device 62, which in this example is a balloon angioplasty device. Single lumen sheath 52 includes a hub 54 with first 56 and second 58 ports and connected to a fluid infusion device 68, and a single lumen 53 having a proximal aperture 66, a distal aperture 64, and two radiopaque markers 51 for facilitating visualization of the proximal aperture 66 location. In this embodiment, renal catheter 60 and vascular catheter 62 are as described previously above, but in various embodiments any suitable alternative devices may be substituted.

A method for using system 50 is much the same as the method described above with reference to FIG. 1. Sheath 52 is placed via a femoral artery using a standard technique or any other desired access technique, such that distal aperture 64 is positioned at or near the ostia of the renal arteries. Renal catheter 60 may then be inserted through first port 56 and advanced through lumen 53 and distal aperture 64 to position its branches 65 within the renal arteries. Before, after or simultaneously with that step, vascular catheter 62 is inserted through second port 58 and advanced through lumen 53 and proximal aperture 66 to extend into the contralateral iliac artery and as far peripherally as desired by the physician. One or more renal substances are then infused into the renal arteries via renal catheter 60, and a radiocontrast substance is infused into the peripheral vessel(s) via vascular catheter 62. In some embodiments, vascular catheter 62 is then used to perform a procedure in one or more vessels. Optionally, infusion device 68 may be used to deliver one or more substances into lumen 53.

FIG. 4 shows single lumen introducer sheath 52 in greater detail. Radiopaque markers 51 may be placed in any of a number of various configurations and locations in various embodiments, to facilitate visualization and localization of proximal aperture 66, distal aperture 64 and/or any other features of sheath 52.

Figure 5:
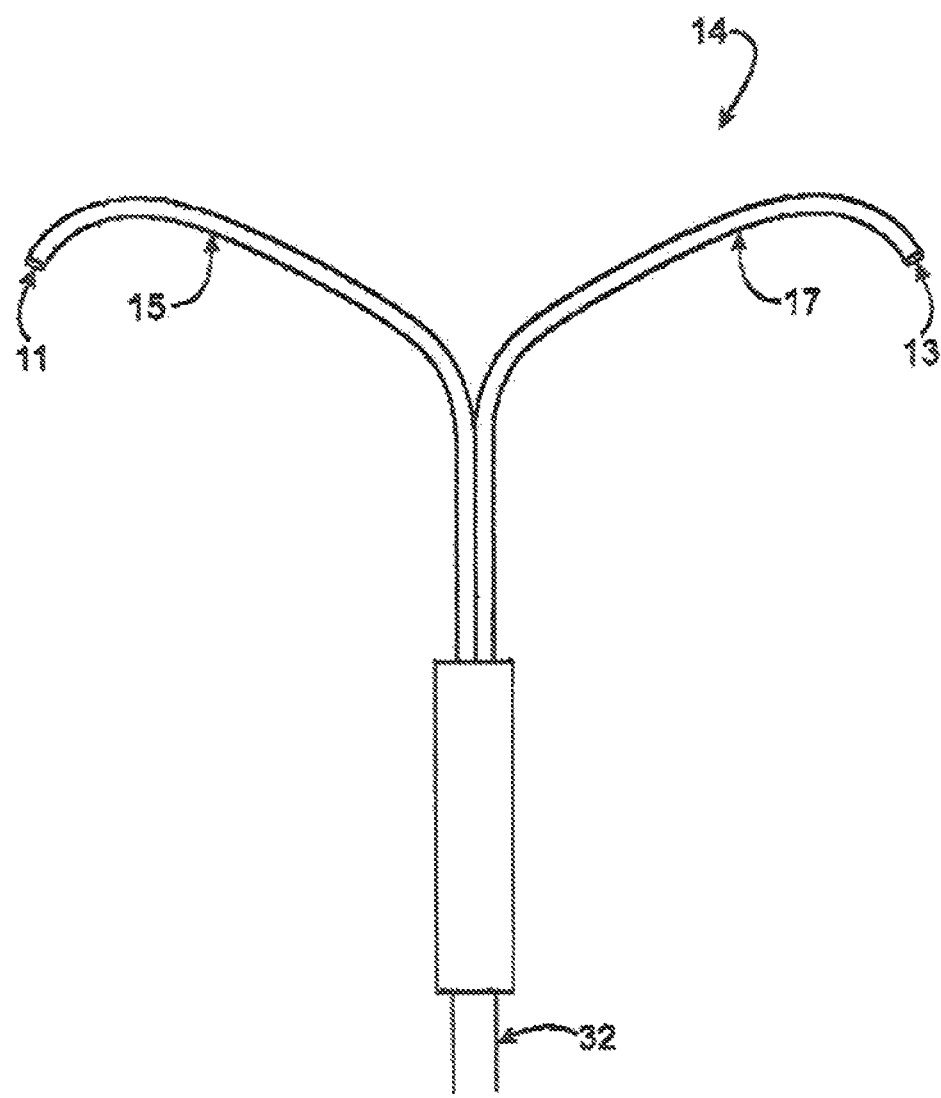
FIG. 5 is a side view of a bifurcated renal artery catheter device for use with a sheath, according to one embodiment.

Referring now to FIG. 5, a distal portion of bifurcated renal catheter 14 includes two branches 15, 17, each including a distal aperture 11, 13, and a proximal catheter body. Each branch 15,17 provides a means to deliver one or more substances to the renal artery in which it is placed. Overall usable length of the renal catheter 14 would generally be such that renal access from a typical femoral artery vascular access point (or other access point) is achieved without an undue length of catheter remaining outside of the patient. Again, various embodiments and features of bifurcated renal catheters are described more fully in U.S. patent application Ser. Nos. 09/724,691, 10/422,624, 10/251,915, 10/636,359 and 10/636,801, and in PCT Patent Application Nos. PCT/US03/029744, PCT/US03/29995, PCT/US03129743 and PCT/US03129585, which were previously incorporated by reference.

Renal catheter 14 may be delivered in a collapsed condition via sheath 12 to the abdominal aorta in the vicinity of the renal arteries. Once deployed, it may expand to contact the walls of the vessel, in an attempt to regain the shape configuration as demonstrated above. This expansion and contraction may be active or passive, as desired, based on the design of renal catheter 14. For the purposes of illustration, the device is considered to be in its free state as pictured in FIG. 3 and compressed via the constraint of the introducer sheath 12 or other means during delivery. Thus renal catheter 14 would "self-expand" upon deployment, to an extent determined by the constraint of the blood vessel. However, renal catheter 14 could alternatively be designed to have the collapsed condition as default and be actively opened once deployed. Such may be accomplished for example by use of integrated pullwires, etc. In any event, the outward contact with the blood vessel (aorta) allows for easy cannulation of multiple vessels, as the device naturally seeks its lower energy state by opening into branch vessels.

When deployed in the aorta, in a procedure where it is desired to access the renal arteries, renal catheter 14 will exit introducer sheath 12, and branches 15, 17 will seek to open to their natural, at-rest state. This will bias branches 15, 17 away from each other and against the inner wall of the vessel, at approximately 180 degrees apart from each other, more or less centering catheter body 32 in the aorta. The proximal end of renal catheter 14 may be manipulated via standard technique (ie., the use of a supplied "torque device" as is common with intravascular guidewires) so that branches 15, 17 are more or less aligned near the target renal arteries' ostia, and with a minimal amount of axial or rotational manipulation, bilateral renal artery cannulation can be achieved.

Previous disclosures by the inventors of the present application have also addressed the merits of various embodiments of bifurcated renal catheters 14 in providing access to multiple vessels simultaneously through a single vascular access point, alone or in combination with other diagnostic or therapeutic interventions or other procedures. For example, such disclosures include U.S. Provisional Patent Application Nos. 60/476,347, filed Jun. 5, 2003; 60/486,206, filed Jul. 9, 2003; 60/502,600, filed Sep. 13, 2003; 60/502,339, filed Sep. 13, 2003; 60/505,281, filed Sep. 22, 2003; 60/493,100, filed Aug. 5, 2003; 601,502,468, filed Sep. 13, 2003; 60/543,671, filed Feb. 9, 2004; 60/550,632, filed Mar. 4, 2004; 60/550,774, filed Mar. 5, 2004; 60/571,057, filed May 14, 2004; 60/612,731, filed Sep. 24, 2004; and 60/612,801, filed Sep. 24, 2004, the full disclosures of which are all hereby incorporated by reference. Similar and alternative embodiments are described in PCT Patent Application Nos.: PCT/US03/029744, filed Sep. 22, 2003; PCT/US04/008573, filed Mar. 19, 2004; PCT/US03/029586, filed Sep. 22, 2003; and PCT/US03/029585, filed Sep. 22, 2003, the full disclosures of which are hereby incorporated by reference.

Bifurcated renal catheter 14 may be similar to that previously described in the above-referenced patent applications or may have any other suitable design and features for bilateral renal cannulation. The example provided and discussed herein for illustration includes, without limitation, a passively self-expanding branched assembly that uses outer sheath constraint to allow delivery to the area of the renal arteries and then expands upon delivery out of the sheath. However, in further embodiments the catheter may also be of the type that is independently collapsible and expandable, if so desired. Various features may be further included. In one particular beneficial embodiment, two distal arms are provided whose shapes and flexibility profile allow for fast bilateral renal artery cannulation with a minimum of required manipulation and such that there is no induced vascular trauma. Exemplary catheter shaft and distal arms may be in the range for example of about 1 Fr. To about 4 Fr. outer diameter. Exemplary arm lengths may be for example in the range of about 2 cm to about 5 cm.

Dimensions and other particular features such as shape, stiffness, etc. may be varied according to the scale of the patient's anatomy, and thus a kit of devices may be provided from which a healthcare provider may chose one particular device to meet a particular need for a particular patient. For example, multiple renal catheters may be provided having small, medium, and large sizes, respectively. Upon being provided a particular patient parameter, such as anatomical dimensions, a person could refer to the device sizes offered and simply match the chosen size to the parameter given. In this regard, a chart may be provided which assists in matching a measured or estimated patient parameter with the appropriate catheter choice.

Although the foregoing is a complete and accurate description of various embodiments of the present invention, any of a number of changes, additions or deletions may be made to one or more embodiments.

Therefore, the foregoing description is provided for exemplary purposes and should not be interpreted to limit the scope of the claims.

The invention claimed is:

1. A method for advancing at least two catheter devices into a vasculature of a patient, the method comprising:
   providing an introducer sheath comprising a proximal end, a distal end, a first proximal port, a second proximal port, at least a first lumen having a distal aperture, and at least a second aperture positioned proximally of the distal aperture;
   positioning the introducer sheath in the patient such that the proximal end is positioned outside the patient, and the distal end is positioned in an abdominal aorta of the patient at or near origins of renal arteries of the patient;
   advancing a renal artery catheter device through the first proximal port to the first distal aperture;
   deploying the renal artery catheter device such that the renal artery catheter device self-expands when advanced from the sheath and cannulates to extend into at least one of the renal arteries; and
   advancing a vascular catheter device through the second proximal port and into at least one peripheral vessel of the patient on a contralateral side of the patient relative to an insertion point of the sheath.

2. A method as in claim 1, further comprising delivering at least one substance into at least one of the renal arteries through the renal artery catheter device.

3. A method as in claim 2, wherein the at least one substance is selected from the group consisting of vasodilators, saline, diuretics, hyper-oxygenated blood, hyper-oxygenated blood substitutes and filtered blood.

4. A method as in claim 2, further comprising delivering at least one additional substance into the at least one peripheral vessel of the patient through the vascular catheter device.

5. A method as in claim 4, wherein the additional substance comprises a radiocontrast agent.

6. A method as in claim 4, further comprising performing an interventional procedure in at least one peripheral vessel of the patient, using the vascular catheter device.

7. A method as in claim 1, wherein the introducer sheath further comprises a second lumen, wherein the second lumen comprises the second aperture, wherein the second aperture is a distal aperture, and wherein the steps of advancing further comprise:
   advancing the renal artery catheter device through the distal aperture of the first lumen; and
   advancing the vascular catheter device through the second distal aperture.

* * * * *